United States Patent [19]

Kumano et al.

[11] 4,189,423

[45] Feb. 19, 1980

[54] PROCESS FOR THE PREPARATION OF POLYOLEFIN MOLDINGS

[75] Inventors: Isao Kumano; Hiromitsu Katsura; Tuneo Tanaka; Takashi Kanno; Shigeru Suzuki, all of Tokyo, Japan

[73] Assignee: Toyo Ink Manufacturing Co., Ltd., Tokyo, Japan

[21] Appl. No.: 929,485

[22] Filed: Jul. 31, 1978

[51] Int. Cl.$^2$ .......................... C08K 5/34; C08K 3/22; C08K 3/30; C08K 3/04
[52] U.S. Cl. .................. 260/42; 260/45.8 N; 260/42.21
[58] Field of Search ......... 260/42.21, 326 N, 45.8 NB

[56] References Cited

U.S. PATENT DOCUMENTS

| | | | |
|---|---|---|---|
| 2,593,840 | 4/1952 | Buc | 260/326 N |
| 3,461,135 | 8/1969 | Gosnell | 260/326 N |
| 3,615,793 | 10/1971 | Sears | 260/326 N X |
| 3,873,567 | 3/1975 | Cyba | 260/45.8 NB |
| 4,001,179 | 1/1977 | Richter et al. | 260/45.8 NB |
| 4,087,441 | 5/1978 | Lee | 260/326 N |

*Primary Examiner*—Sandra M. Person
*Attorney, Agent, or Firm*—Frank J. Jordan

[57] ABSTRACT

A process for producing a dimensionally stable polyolefin molding, characterized by using a specific compound or a mixture thereof with at least one ordinary pigment, the specific compound being obtained by reacting a halogenated phthalic compound with hydrazine or an organic diamine.

6 Claims, 1 Drawing Figure

U.S. Patent
Feb. 19, 1980
4,189,423
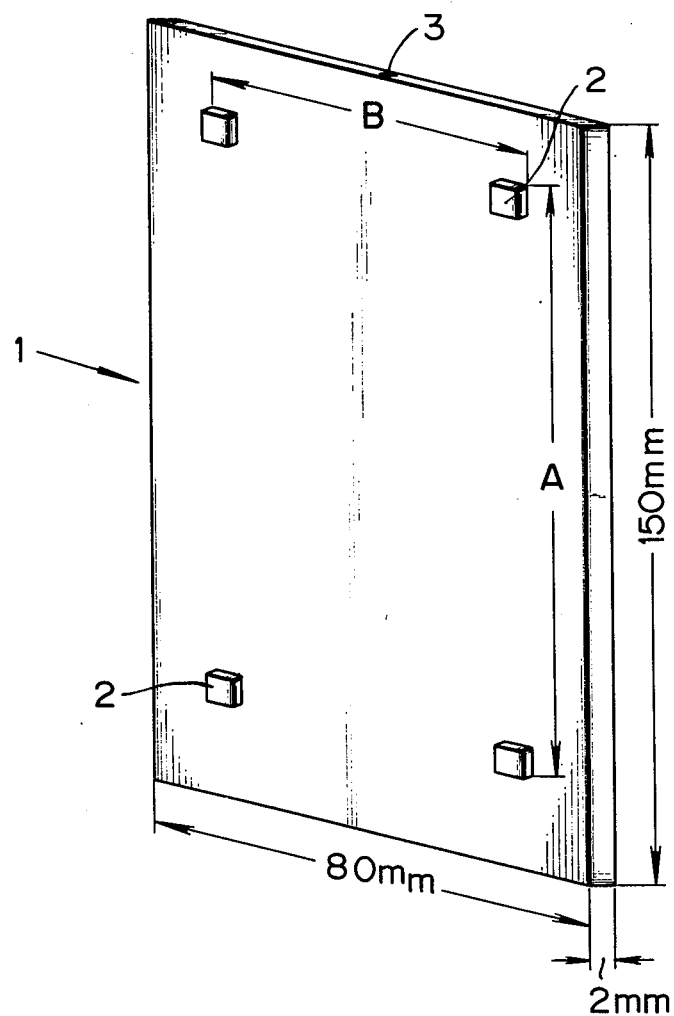

PROCESS FOR THE PREPARATION OF POLYOLEFIN MOLDINGS

This invention relates to a novel process for preparing polyolefin moldings and more particularly it relates to a novel process for preparing polyolefin modings having excellent dimensional stability substantially without any dimensional change and consequent distortion of the moldings.

Among polyolefins, a high density polyethylene obtained by a Ziegler's process is a crystalline polymer which is of straight-chain molecular structure and finds its wide use in many fields because of its excellence in various properties, however, if the polyethylene is melted and molded then the resulting molding will not only shrink into a small size as compared with the mold used, but also vary in degree of shrinkage directionally with respect to the direction of flow of the melted polyethylene at the time of the molding since the polyethylene is liable to crystallize and change in volume due to its phase change during the molding. Since, particularly in the injection molding of the polyethylene, the crystallized portions of the polyethylene is liable to be oriented in the direction of flow thereof and the directionality tends to take place in the resulting molding. Thus, it is necessary to take such shrinkages into account in order to produce dimensionally stable moldings.

These disadvantages such as shrinkage and directionality will usually take place on a colored resin molding when it is produced from a resin incorporated with an inorganic and/or organic pigment for coloring the resin, and they will be remarkable depending on the kind of the pigment or pigments used. On the other hand, it has been customary that moldings produced from polyolefins containing no pigments will differentiate in dimension from a mold used because of their shrinkage after the molding and that molds and injection molding conditions are required to be previously adjusted thereby to offset the particular shrinkage of polyethylene, polypropylene, A.B.S., polystyrene, polyvinyl chloride or the like each time any one of them is used, this being very inconvenient.

After various studies made by the present inventors in attempts to solve problems as to the dimensional accuracy on polyolefin moldings, it has been found that the problems may be solved by incorporating at least one compound in a resin alone or a mixture thereof with at least one ordinary pigment when the resin or mixture is melted and molded, the at least one compound being represented by the following general formula (I)

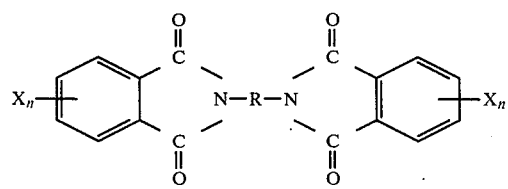

wherein

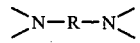

is the residue of hydrazine or an organic diamine, X is a halogen atom and n is an integer of from 0 to 4.

The compounds (I) according to this invention are effective in solving the problem that when polyolefins are molded, they not only shrink into a finish size smaller than the predetermined size since they change in volume at the time of their phase change from molten state to solid molded state, but also vary in degree of shrinkage directionally with respect to the direction of flow of the molten polyolefins during the molding and cause distortion in the resulting moldings depending on the shape thereof. Thus, the compounds (I) are excellent as a dimensional stabilizer in stabilizing the resulting moldings dimensionally.

The use of the compound (I) in the molding of resins such as polyolefins will prevent the resulting moldings from decreasing in finish size as compared with the mold used and will also enable polyolefins to be molded with the same mold under the same molding conditions by decreasing the difference in amount of shrinkage between one resin and another in view of the fact that molds and molding conditions have heretofore been selected depending on the quality of a resin used.

The compounds (I) according to this invention will have no adverse effects on the color of colored polyolefin moldings when these moldings are produced from polyolefins incorporated with the compound (I) together with or without a pigment.

The compounds (I) according to this invention may be produced in colorless or slightly colored state because of their chemical structure and they may therefore be used, together with a pigment, in coloring polyolefins with the pigment without having adverse effects on the color of polyolefin moldings to be produced, thereby rendering it possible to obtain polyolefin moldings having a clear color. Further, it should particularly be noted that the compounds (I) will counteract the remarkable adverse effects of at least one conventional or ordinary inorganic and/or organic pigment on the dimensional accuracy of polyolefin moldings when these moldings contain the compound (I) and at least one ordinary pigment for coloration thereof. Accordingly, this invention enables various ordinary pigments which have been thought to have adverse effects on the dimensional accuracy of polyethylene or other polyolefin moldings when these moldings contain at least one such pigment, to be used in producing colored polyolefin moldings substantially without adversely affecting the dimensional accuracy thereof by adding the compound (I), together with the ordinary pigment or pigments to polyolefin to be molded. More particularly, when carbon black, titanium dioxide, cadmium yellow, cadmium red, Prussian blue, rouge or the like is added in any amounts as an inorganic pigment to polyolefin to be molded, the inorganic pigment will allow the resulting colored polyolefin moldings to have about the same dimensional accuracy as the corresponding non-colored polyolefin moldings (containing no pigments) and, therefore, it may of course be used as a colorant for polyolefins to be molded, together with the compound (I).

Flavanthrone, anthrapyrimidine yellow, brominated anthrone, indanethrone and other anthraquinone pigments, polyazo pigments, isoindolinone pigments, perylene pigments, quinacridone pigments, copper phthalocyanine blue or green and other phthalocyanine pigments, and the like are excellent in endurance, color tone, tinting strength and the like but they have heretofore not satisfactorily been used as a colorant for polyolefins to be molded since even if these organic pigments be added in small amounts to polyolefins (such as polyethylene) to be molded, they will cause the resulting colored polyolefin moldings to shrink in such a specific manner that the degree of shrinkage in the direction of flow of the polyolefin resin is different from that in the direction perpendicular to said polyolefin resin flow direction. However, this invention makes it possible to use all of the organic pigments as a satisfactory colorant for polyolefins to be molded, by using the compound (I) according to this invention together with the organic pigments.

This invention may be evaluated to have a great advantage from the view-point of industrial production of colorants for polyolefins. The great advantage is that a process for the production of colorants for polyolefins to be molded may be remarkably simplified as mentioned below.

There have heretofore been proposed processes for the specific synthesis or after treatment of a pigment and processes for the improvement of a pigment by the addition of a dimension accuracy improver thereto (Japanese Patent Appln. Laying-Open Gazettes Nos. 101440/75, 134042/75, 18551/75, 71736/75, 58447/76 and 74039/76 for example), however, it is considered that, to meet the requirements for the production of polyolefin moldings in various colored state, an industrialized process for the production of colored polyolefin moldings should include from a process for the production of pigments to a process for the production of specific colorants for polyolefins. Thus, raw materials for the colorants as well as the steps of production thereof are very complicated. Simplified processes for the same purpose have been sought, accordingly.

According to this invention, such a simplified process may be realized only by adding a necessary amount of the compound (I), together with a dispersant and the like, to a mixture of polyolefin and a conventional pigment at the time of blending the mixture.

The compound (I) according to this invention represented by the general formula (I) may be obtained by a method comprising dehydration reacting a halogenated phthalic anhydride with hydrazine or an organic diamine in an inert organic solvent or by a method comprising heating the potassium salt of a halogenated phthalimide and a saturated or unsaturated hydrocarbon or an aryl compound substituted with two halogen atoms in a polar organic solvent (this being the so-called Gabriel synthesis); said substituted hydrocarbon includes dibromoethane, dibromoethylene, dichloroethane, dibromopropane, dichloropropane, dibromohexane or dichlorohexane, and the aryl compound includes dibromobenzene, dichlorobenzene, dibromonaphthalene or dichloronaphthalene. Each of these methods may produce the compound (I) in high purity and in a high yield, however, the method using the halogenated phthalic anhydride and hydrazine or the organic diamine is preferred from the view-point of manufacture and availability of the starting materials, cost of the solvent, recovery of the used solvent, and the like.

With respect to the dimensional change of polyolefins, such as polyethylene, at the time of molding thereof, the impurities contained in the polyolefins have remarkable effects on the dimensional change thereof, and the impurities produced as a by-product by the aforesaid reaction are removed effectively by cleaning them with an aprotic dipolar solvent such as N,N-dimethylformamide thereby further enhancing the dimensional change-preventing effects.

The process for the production of the compound (I) will be detailed in Preparations 1–10 to be described later.

The inert solvents which may preferably be used in this invention include halogenated benzenes such as monochlorobenzene, dichlorobenzene, trichlorobenzene and monobromobenzene; nitrated benzenes such as nitrobenzene, nitrotoluene and chloronitrobenzene; alkylbenzenes such as toluene, xylene, ethylbenzene, isopropylbenzene, isopropyltoluene, diisopropyltoluene, isopropylxylene, butylbenzene, acylbenzene, dodecylbenzene, decaline and tetralin; ether type solvents such as anisole, phenetole and diphenyl ether; ketonic solvents such as acetophenone and benzophenone; ester type solvents such as methyl benzoate and ethyl benzoate; and other compounds such as diphenylmethane, diphenylethane, chloronaphthalene, nitronaphthalene, pyridine, quinoline, N,N-dimethylformamide and dimethylsulfoxide.

The aprotic dipolar solvents which may be used in Gabriel method include dioxane, N,N-dimethylformamide, dimethylsulfoxide, α-pyrrolidone, methyl isobutyl ketone, anisole, ethylene glycol, and methyl and ethyl benzoates with N,N-dimethylformamide, α-pyrrolidone and dimethylsulfoxide being particularly preferred from the view-point of reaction time, yield, purity and the like.

The compounds (I) according to this invention are very satisfactory in resistances such as heat resistance, weather-proofing property and chemical resistance and will not change in chemical structure and crystal structure even if subjected to treatments at high temperatures and pressures as in the molding of polyolefins and the like. In the compound (I) having been highly halogenated per molecule, the surface of the crystal is mostly covered with halogen atoms and, therefore, the state thereof is expected to have properties which are similar to those of inorganic matter rather than organic matter.

It is not clear what causal relation lies between the use of the compound (I) and the inhibition of dimensional change of a polyolefin molding to be obtained in the case of molding a polyolefin incorporated with the compound (I), however, it is considered from the aforesaid properties of the compound (I) that the compound (I) will have some specific effects, which are different from those of other organic compounds, on the crystallization of polyolefins such as polyethylene.

There will then be detailed various problems as to the process of this invention for the production of polyolefin moldings. The compound (I) according to this invention may be used alone or jointly with a dye or pigment and various additives. The use of the compound (I) in an amount of 0.0001% by weight of polyolefin such as polyethylene will prevent a dimensional change, distortion or the like due to the specific crystallization of the polyolefin. Further, the use of the compound (I) in an amount of as small as 1% or more by weight of at least one of the aforesaid organic compounds which have heretofore been difficult to use because they cause distortion on the resulting polyolefin moldings containing the organic compound, will substantially prevent the distortion and the like which would otherwise be caused in polyolefin moldings obtained by using the organic compounds alone (without the use of the compound (I)).

In addition to the known inorganic and organic pigments which may be used as the aforesaid colorants, there may be used as extenders barium sulphate, barium carbonate, calcium carbonate, silica, clay, alumina, talc and the like. Other additives which may generally be used in the molding of polyolefins include various surface active agents, plasticizers, dispersants, stabilizers, antioxidants, ultraviolet light absorbers and antistatic agents.

The compounds (I) are obtained in colorless or slightly colored powder form and, depending on the purpose for which they are to be used, they may be used in the form of a paste obtained by incorporating an organic solvent, liquid plasticizer or the like thereinto, in the form of an concentrate obtained by kneading various resins therewith, in the form of an article obtained by mixing therewith a carrier material such as a low density polyethylene or polypropylene, or in other forms.

The resins which may be used in this invention include polyethylene, polypropylene, mixtures thereof, polystyrene. The main polyolefin to which this invention is the most effectively applicable, is polyethylene since medium or low pressure polyethylenes are liable to raise problems as to dimensional accuracy. The compound (I), resins, pigments and other additives may be mixed together mainly by melt kneading. Manual tumbling, a tumbler, a high speed mixer, kneading with rolls and kneading with a kneader may be used as a preliminary mixing means. Further, colored pellets, dry color, master batches and the like intended for preliminary dispersion of the starting materials may also be used as a preliminary mixing means.

Polyolefins, the compound (I), colorants and additives may be molded by, for example, injection molding, extruding molding, blow molding or vacuum molding.

The compound (I) is not particularly limited in amount used and it will exhibit satisfactory effects even if it is used in an amount of less than 1% by weight of a resin used together with the compound (I). Thus, the compound (I) may vary in amount used depending on the properties of a pigment used as a colorant together therewith and may be used in the range of 0.0001 to 1% by weight of the resin.

The compounds (I) may be prepared as shown in the following Preparations 1 to 10 wherein all parts are by weight unless otherwise specified.

PREPARATION 1

14.3 parts (0.05 mol) of tetrachlorophthalic anhydride and 4.0 parts (0.025 mol) of 1,5-naphthalenediamine were thoroughly suspended in 100.0 parts of nitrobenzene and reacted together under agitation at 170° to 180° C. for 5 hours while removing the water produced as a by-product from the reaction system, to obtain a reaction mixture. The thus obtained reaction mixture was cooled to room temperature, freed from the precipitates by filtration and then thoroughly washed with methanol to obtain 17.0 parts of a greyish-white crystal represented by the following formula (I-1)

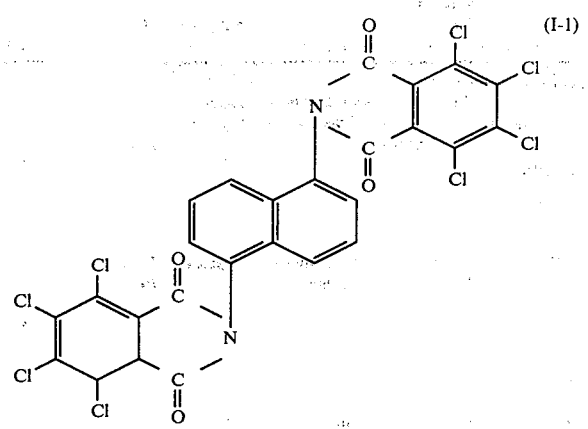

PREPARATION 2

23.3 parts (0.05 mol) of tetrabromophthalic anhydride and 2.9 parts (0.025 mol) of hexamethylenediamine were thoroughly suspended in 80 parts of o-dichlorobenzene and then heated. The whole mass was further heated to 160°-170° C. for 5 hours while removing the water produced as a by-product from the reaction system to obtain 24.5 parts of a light yellow crystal. The crystal so obtained was treated in 245 parts of N,N-dimethylformamide under reflux at elevated temperature for 5 hours, after which the whole mass was cooled to room temperature and the crystal was separated therefrom. The crystal so separated was thoroughly washed with methanol to obtain 24 parts of a light yellow crystal represented by the following formula

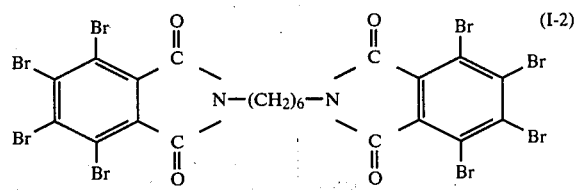

PREPARATIONS 3-10

In each of Preparations 3-10, the procedure of Preparation 1 was followed except that a new combination of starting compounds was substituted for the combination in Preparation 1. The new combinations and the phthalimide compounds obtained are indicated in Table 1.

Table 1

| Preparation No. | Phthalic anhydride and Halogenated phthalic anhydride | Diamine | Reaction solvent | Appearance of product | Chemical structure of product | Formula No. |
| --- | --- | --- | --- | --- | --- | --- |
| 3 | Monochlorophthalic anhydride | m-phenylene diamine | Isobutylbenzene | Greyish white crystal | | I-3 |

Table 1-continued

| Preparation No. | Phthalic anhydride and Halogenated phthalic anhydride | Diamine | Reaction solvent | Appearance of product | Chemical structure of product | Formula No. |
|---|---|---|---|---|---|---|
| 4 | Dichlorophthalic anhydride | 4,4'-diaminodiphenylmethane | Dodecyl benzene | Light yellow crystal | 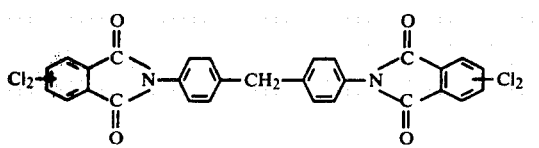 | I-4 |
| 5 | Trichlorophthalic anhydride | 3,6-diaminoacridine | Decalin | Light brown crystal | 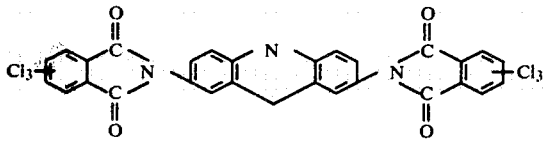 | I-5 |
| 6 | Dibromophthalic anhydride | Benzidine | Amylbenzene | Light yellow crystal | 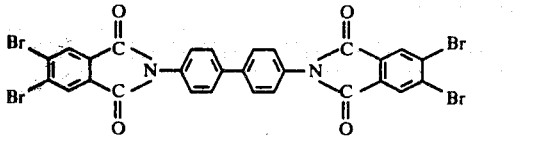 | I-6 |
| 7 | Tetrachlorophthalic anhydride | 3,3'-diaminodiphenyl ether | Diphenyl ether | Light Yellow crystal | 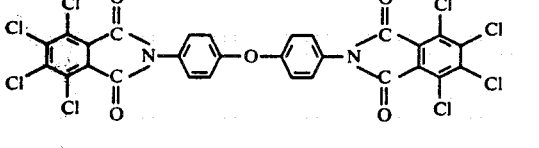 | I-7 |
| 8 | Tetrachlorophthalic anhydride | 3,3'-diaminodiphenylsulfone | Dimethyl sulfoxide | Light yellow crystal | 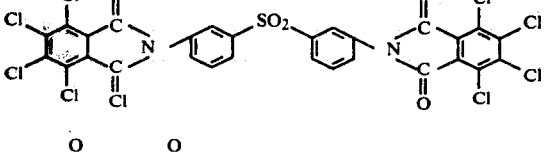 | I-8 |
| 9 | Phthalic anhydride | Hydrazine | Xylene | Light yellow crystal | 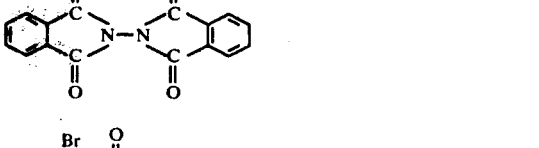 | I-9 |
| 10 | Tetrabromophthalic anhydride | 1,5-napthalene diamine | Isopropyl toluene | Yellowish white crystal | 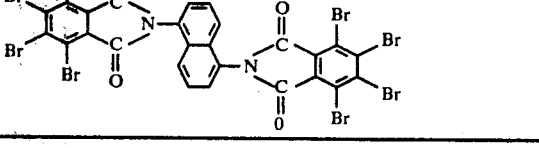 | I-10 |

Preparation 11

25.2 parts (0.05 mol) of potassium salt of tetrabromophthalimide and 6.1 parts (0.025 mol) of 1,6-dibromohexane were heated to 145°–150° C. under agitation for 5 hours in 100 parts of N,N-dimethylformamide to obtain a reaction mixture, from which a crystal was separated and thoroughly washed with methanol to obtain 24.5 parts of the same light yellow crystal (formula (I-2)) as obtained in Preparation 2.

For comparison with this invention, comparative examples in which conventional pigments were used are indicated hereinunder.

Comparative examples 1–18

A high density polyethylene (produced under the trademark of HIZEX 2208-J by Mitsui Petrochemicals) alone, a polypropylene (produced under the trademark of NOBLEN BC-8 by Mitsubishi Yuka Co.) alone and blends of each of the polyethylene and polypropylene with various pigments, were molded by an injection molder (produced under the trademark of IS80A by Toshiba Machinery Works) under the conditions: molding temperature, 260° C; cylinders $C_1$, $C_2$ and $C_3$ respectively at 230° C., 240° C. and 250° C.; mold, 50° C.; and injection pressure 80 Kg/cm² (Gauge pressure). The mold used was such that a resin injection plate as shown in FIG. 1 was obtained by the use thereof.

FIG. 1 shows an injection plate for measuring the shrinkage thereof, in which the injection plate is generally indicated at numeral 1, protrusions for defining the length to be measured are indicated at numeral 2 and a gate is indicated at 3. The injection plates obtained by the use of said mold were tested for their shrinkages after the lapse of one week from the time of manufacture of the injection plates. The results are shown in Tables 2 and 3. Measurement for shrinkage:

The injection plates after the lapse of one week from the time of manufacture thereof, were measured for their shrinkage. To this end, the lengths A (the corresponding length A of the mold being 120 mm) and B (the corresponding length of the mold being 60 mm) of the injected plates as shown in FIG. 1 were measured. The symbol A also indicates the direction of flow of the polymer and the symbol B the direction perpendicular to the direction A. Assuming that the lengths A and B found by the measurement are LA (mm) and LB (mm) respectively and that the shrinkages in the directions of A and B are SA and SB respectively, $$SA = (120 - LA/120) \times 100\%$$

$$SB = (60 - LB/60) \times 100\%$$

$$SA/SB = \text{Shrinkage ratio}$$

the organic pigment alone or the use of a mixture of the organic and inorganic pigments is disadvantageous in that the shrinkage in the direction A is greater than that in the direction B thereby lowering the dimensional accuracy. In addition, the finish dimensions were found to decrease as compared with the intended ones in the Comparative examples in which the polyethylene was used as the polyolefin material.

This invention will further be explained by reference to the following examples.

EXAMPLES 1-34

The procedure of the Comparative examples was followed except that any one of the compounds (I-1) to (I-10) was additionally used. The results are shown in Tables 4 and 5.

From the comparison between Tables 2 and 4 as well as between Tables 3 and 5, it is seen that the use of the polyolefin and compound (I), the use of the polyolefin, compound (I) and organic pigment and the use of the polyolefin, compound (I), organic pigment and inorganic pigment resulted in the production of the polyolefin moldings having excellent dimensional accuracy as compared with the use of the organic pigment alone. Particularly, the use of the compound (I) alone as the pigment resulted in the production of the polyolefin having a less reduced dimension as the finish dimension

| Com. ex. | Pigment used in polyethylene | Amount of pigment used (%) | SA (%) | SB (%) | Shrinkage ratio |
|---|---|---|---|---|---|
| 1 | None (polyethylene alone) | — | 2.21 | 1.91 | 1.16 |
| 2 | Titanium dioxide | 0.4 | 2.26 | 1.87 | 1.21 |
| 3 | Cadmium yellow | 0.4 | 2.24 | 1.90 | 1.18 |
| 4 | Cadmium red | 0.4 | 2.25 | 1.91 | 1.18 |
| 5 | Phthalocyanine blue (Stable type) | 0.1 | 3.90 | 1.83 | 2.13 |
| 6 | Phthalocyanine blue (Unstable type) | 0.1 | 3.95 | 1.80 | 2.19 |
| 7 | phthalocyanine green | 0.1 | 3.77 | 1.83 | 2.02 |
| 8 | Quinacridone red | 0.1 | 3.70 | 1.83 | 2.06 |
| 9 | Isoindolinone yellow | 0.1 | 3.89 | 1.83 | 2.13 |
| 10 | Perylene red | 0.1 | 3.93 | 1.81 | 2.17 |
| 11 | Bromated anthanthrone | 0.1 | 3.65 | 1.82 | 2.01 |
| 12 | Titanium dioxide + phthalocyanine blue (70:30) | 0.3 | 3.61 | 1.82 | 1.98 |

Table 3

| Com. ex. | Pigment used in polyethylene | Amount of pigment used (%) | SA (%) | SB (%) | Shrinkage ratio |
|---|---|---|---|---|---|
| 13 | None (polypropylene alone) | — | 1.75 | 1.67 | 1.05 |
| 14 | Cadmium red | 0.4 | 1.77 | 1.63 | 1.09 |
| 15 | Titanium dioxide | 0.4 | 1.76 | 1.65 | 1.07 |
| 16 | Phthalocyanine blue (Stable type) | 0.1 | 1.98 | 1.58 | 1.25 |
| 17 | Phthalocyanine green | 0.1 | 1.92 | 1.52 | 1.26 |
| 18 | Quinacridone | 0.1 | 2.01 | 1.61 | 1.25 |

Note:
Com. ex.: Comparative example

It is seen from Tables 2 and 3 that the use of the inorganic pigment as the colorant gave approximately the same shrinkage as the non-use of pigments (non-colored polyethylene and polypropylene), while the use of as is apparent from the values of SA and SB in Table 4; this tendency is approximately similar to that in the case of the use of the compound (I) in the polypropylene as shown in Table 5.

Table 4

| Example No. | Pigment(s) used | | Amount of pigment or pigments used | SA (%) | SB (%) | Shrinkage ratio |
|---|---|---|---|---|---|---|
| 1 | Compound (I-1) | | 0.01 | 1.82 | 1.77 | 1.03 |
| 2 | " | | 0.1 | 1.73 | 1.68 | 1.03 |
| 3 | Phthalocyanine blue + Compound (I-1) | (90 : 10) | 0.1 | 2.35 | 1.84 | 1.28 |
| 4 | Compound (I-2) | | 0.1 | 1.92 | 1.80 | 1.07 |

Table 4-continued

| Example No. | Pigment(s) used | Amount of pigment or pigments used | | SA (%) | SB (%) | Shrinkage ratio |
|---|---|---|---|---|---|---|
| 5 | Quinachridone red + Compound (I-2) | (95 : 5) | 0.1 | 2.21 | 1.80 | 1.20 |
| 6 | Phthalocyanine green + Compound (I-3) | (80 : 20) | 0.1 | 2.10 | 1.92 | 1.09 |
| 7 | Isoindolinone yellow + (I-3) | (90 : 10) | 0.1 | 2.29 | 1.90 | 1.20 |
| 8 | Compound (I-4) | | 0.1 | 1.91 | 1.79 | 1.07 |
| 9 | Compounds (I-4) + Compound (I-5) | (85 : 15) | 0.1 | 2.10 | 1.85 | 1.13 |
| 10 | Perylene red + Compound (I-4) | (90 : 10) | 0.1 | 2.05 | 1.88 | 1.09 |
| 11 | Quinachridone red + Compound (I-5) | (95 : 5) | 0.1 | 2.15 | 1.95 | 1.10 |
| 12 | Phthalocyanine blue + Compound (I-6) | (90 : 10) | 0.1 | 2.25 | 1.75 | 1.29 |

Table 5

| Example No. | Pigment(s) used | Amount of pigment or pigments used | | SA (%) | SB (%) | Shrinkage ratio |
|---|---|---|---|---|---|---|
| 20 | Compound (I-1) | | 0.01 | 1.65 | 1.58 | 1.04 |
| 21 | " | | 0.1 | 1.49 | 1.40 | 1.06 |
| 22 | Phthalocyanine blue + Compound (I-1) | (90 : 10) | 0.1 | 1.80 | 1.45 | 1.24 |
| 23 | Phthalocyanine blue + Compound (I-2) | (95 : 5) | 0.1 | 1.82 | 1.50 | 1.21 |
| 24 | Phthalocyanine green + Compound (I-1) | (95 : 5) | 0.1 | 1.75 | 1.43 | 1.22 |
| 25 | Compound (I-3) | | 0.1 | 1.60 | 1.48 | 1.08 |
| 26 | Quinacridone red + Compound (I-3) | (85 : 15) | 0.1 | 1.78 | 1.51 | 1.18 |
| 27 | Phthalocyanine blue + Compound (I-4) | (90 : 10) | 0.1 | 1.84 | 1.52 | 1.21 |
| 28 | Isoindolinone yellow + Compound (I-5) | (90 : 10) | 0.1 | 1.78 | 1.49 | 1.19 |
| 29 | Compound (I-5) | | 0.1 | 1.59 | 1.43 | 1.11 |
| 30 | Isoindolinone yellow + Compound (I-5) | (95 : 5) | 0.1 | 1.81 | 1.53 | 1.18 |
| 31 | Perylene red + Compound (I-6) | (90 : 10) | 0.1 | 1.77 | 1.48 | 1.19 |
| 32 | Isoindolinone yellow + Compound (I-9) | (90 : 10) | 0.1 | 1.80 | 1.51 | 1.19 |
| 33 | Compound (I-10) | | 0.1 | 1.55 | 1.51 | 1.03 |
| 34 | Phthalocyanine blue + Compound (I-10) | (90 : 10) | 0.1 | 1.76 | 1.53 | 1.15 |

(Polypropylene NOBLEN BC-8)

What is claimed is:

1. In a process for producing a dimensionally stable polyolefin molding, the improvement comprising the use of a member selected from the group consisting of (A) at least one compound (I) as the dimensional stabilizer and (B) a mixture of the at least one compound (I) with at least one ordinary pigment as the colorant, the at least one compound (I) being represented by the following general formula:

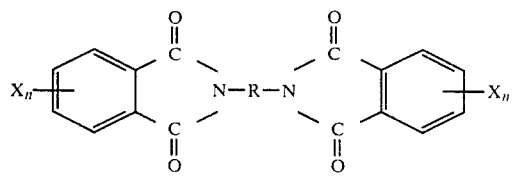

wherein

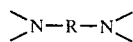

is the residue of an organic diamine containing 1 to 3 aromatic rings, X is a halogen atom and n is an integer from 1 to 4, said compound (I) being used in an amount of 0.0001% to 1% by weight of polyolefin.

2. A process according to claim 10 wherein the compound (I) is a compound represented by the following formula

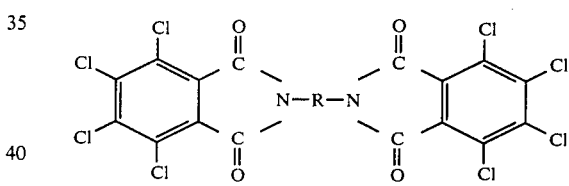

wherein

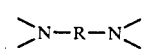

is as defined above.

3. A process according to claim 10, wherein the compound (I) is a compound represented by the following formula

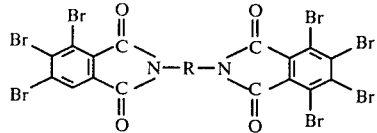

wherein

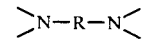

is as defined above.

4. A process according to claim 10, wherein the organic diamine is a member selected from the group consisting of m-phenylenediamine, 4,4'-diaminodiphenylmethane, 3,6-diaminoacridine, benzidine, 4,4'-diaminodiphenyl ether, 3,3'-diaminodiphenylsulfone, 1,5-naphthalenediamine, and p-phenylenediamine.

5. A process According to claim 4, wherein the ordinary pigment is a compound selected from the group consisting of carbon black, titanium dioxide, cadmium yellow, cadmium red, Prussian blue and iron oxide.

6. A process according to claim 4, wherein the ordinary pigment is a compound selected from the group consisting of anthraquinone pigments, polyazo pigments, phthalocyanine pigments, quinacridone pigments and isoindolinone pigments.

* * * * *